(12) United States Patent
Jardinier et al.

(10) Patent No.: US 9,285,304 B2
(45) Date of Patent: Mar. 15, 2016

(54) OPTICAL WAVEGUIDE COMPRISING A NANO-CHANNEL AND OPTOFLUIDIC SENSOR USING SUCH AN OPTICAL WAVEGUIDE

(71) Applicant: COMMISSARIAT A L'ENERGIE ATOMIQUE ET AUX ENERGIES ALTERNATIVES, Paris (FR)

(72) Inventors: Elsa Jardinier, Grenoble (FR); Laurent Couston, Villeneuve les Avignon (FR); Jean-Emmanuel Broquin, Grenoble (FR); Davide Bucci, Grenoble (FR); Fabrice Canto, Les Angles (FR); Alastair Magnaldo, Connaux (FR)

(73) Assignee: Commissariat à l'énergie atomique et aux énergies alternatives, Paris (FR)

( * ) Notice: Subject to any disclaimer, the term of this patent is extended or adjusted under 35 U.S.C. 154(b) by 0 days.

(21) Appl. No.: 14/647,580

(22) PCT Filed: Nov. 26, 2013

(86) PCT No.: PCT/EP2013/074708
§ 371 (c)(1),
(2) Date: May 27, 2015

(87) PCT Pub. No.: WO2014/082988
PCT Pub. Date: Jun. 5, 2014

(65) Prior Publication Data
US 2015/0300943 A1    Oct. 22, 2015

(30) Foreign Application Priority Data
Nov. 27, 2012   (FR) ..................................... 12 61285

(51) Int. Cl.
*G01N 21/03*         (2006.01)
*G01N 21/31*         (2006.01)
(Continued)

(52) U.S. Cl.
CPC ...... *G01N 21/0303* (2013.01); *B01L 3/502715* (2013.01); *G01N 21/31* (2013.01);
(Continued)

(58) Field of Classification Search
USPC ............................................... 385/14–24, 147
See application file for complete search history.

(56) References Cited

U.S. PATENT DOCUMENTS 6,310,995 B1 * 10/2001 Saini ...................... B82Y 20/00
                                                  385/28
7,444,045 B2 * 10/2008 Fan ...................... G01N 21/552
                                                  385/123

(Continued)

FOREIGN PATENT DOCUMENTS

WO    WO 2007/137157 A2    11/2007
WO    WO 2008/073967 A1     6/2008

OTHER PUBLICATIONS

International Search Report issued Jan. 22, 2014, in PCT/EP2013/074708, filed Nov. 26, 2013.

(Continued)

*Primary Examiner* — Akm Enayet Ullah
(74) *Attorney, Agent, or Firm* — Oblon, McClelland, Maier & Neustadt, L.L.P (57) ABSTRACT

An optical waveguide including a first substrate incorporating a first optical guiding structure exposed at a surface of the first substrate, a second substrate incorporating a second optical guiding structure exposed at a surface of the second substrate, the two substrates being assembled superimposed by their surfaces such that the two optical guiding structures are facing each other and extend in a same direction. A channel is fitted between the first and the second guiding structure, directed along the direction, the channel having a cross-section with a large dimension substantially parallel to the surface of the first substrate and to the surface of the second substrate, enabling light to interact on a given distance with the fluid. Such a waveguide can, for example, find application to fluid analysis.

16 Claims, 6 Drawing Sheets

(51) Int. Cl.
*B01L 3/00* (2006.01)
*G02B 6/122* (2006.01)
*B82Y 20/00* (2011.01)
*G01N 21/552* (2014.01)
*G01N 21/77* (2006.01)

(52) U.S. Cl.
CPC ...... *G02B 6/1223* (2013.01); *B01L 2300/0654* (2013.01); *B01L 2300/0877* (2013.01); *B01L 2300/0887* (2013.01); *B01L 2300/161* (2013.01); *B82Y 20/00* (2013.01); *G01N 21/552* (2013.01); *G01N 21/7703* (2013.01); *G01N 21/7746* (2013.01); *G01N 2201/08* (2013.01)

(56) References Cited

U.S. PATENT DOCUMENTS

| | | | | |
|---|---|---|---|---|
| 7,519,257 B2* | 4/2009 | Lipson | | B82Y 20/00 385/126 |
| 7,609,932 B1* | 10/2009 | Spillane | | G02B 6/105 385/1 |
| 7,894,696 B2* | 2/2011 | Baehr-Jones | | B82Y 20/00 385/1 |
| 8,547,542 B2 | 10/2013 | Couston et al. | | |
| 2002/0090160 A1* | 7/2002 | Lim | | B82Y 20/00 385/11 |
| 2004/0202429 A1* | 10/2004 | Margalit | | B82Y 20/00 385/49 |
| 2006/0228074 A1 | 10/2006 | Lipson et al. | | |
| 2008/0152279 A1 | 6/2008 | Feng et al. | | |
| 2009/0015906 A1 | 1/2009 | Kimerling et al. | | |
| 2010/0002994 A1 | 1/2010 | Baehr-Jones et al. | | |
| 2010/0091358 A1 | 4/2010 | Kimerling et al. | | |

OTHER PUBLICATIONS

French Preliminary Search Report issued Aug. 13, 2013, in Patent Application No. FR 1261285, filed Nov. 27, 2012 (with English Translation of Category of Cited Documents).

C. A. Barrios, et al., "Compact silicon slot-waveguide disk resonator", Technical Digest CD-ROM/Conference on Lasers and Electro-Optics, Quantum Electronics and Laser Science Conference, Conference on Photonic Applications, Systems and Technologies, XP 031394363, May 21, 2006, 2 pages.

* cited by examiner

OPTICAL WAVEGUIDE COMPRISING A NANO-CHANNEL AND OPTOFLUIDIC SENSOR USING SUCH AN OPTICAL WAVEGUIDE

TECHNICAL FIELD

The present invention relates to an optical waveguide comprising a nano-channel and to an optofluidic sensor using such an optical waveguide. Such a sensor is usable for example for fluid chemical, biological, biochemical or physical analysis in particular in a hostile environment. The miniaturization of sensors for fluid analysis makes the reduction of the quantity of the fluid to use possible, this being significant in particular if the fluid is radioactive. Fluid samples used then have a reduced radioactive activity and reduced response times. This is also significant for analyses where the fluid comes from procedures producing very limited volumes, as chromatographic fractions, or liquid-liquid extraction procedures. These optofluidic sensors use absorption spectrometry. The measurement of absorption spectra is widely used in any scientific fields ranging from industry to research.

Absorption spectrometry is based on the capacity of chemical species to absorb light at some wavelengths. It is described by the Beer-Lambert Law which is expressed by $P=P_0 \exp(-\lceil \alpha \lfloor)$ with:

$P_0$ power of light at the input of the optical waveguide,
P power of light transmitted into the optical waveguide,
$\alpha$ absorption coefficient of the fluid to be analysed, $\alpha = \epsilon c$ with $\epsilon$ coefficient of molar extinction of the fluid to be analysed and c concentration of the fluid to be analysed,
$\lceil$ interaction factor of light with the fluid and
$\lfloor$ interaction length between the fluid, and light.

It is to be noted that the optical waveguide comprising a nano-channel could also be used in the field of telecommunications, in this case the channel would be filled with a fluid enabling a guided optical signal to be modulated and/or filtered and/or amplified.

STATE OF PRIOR ART

Figure 1:
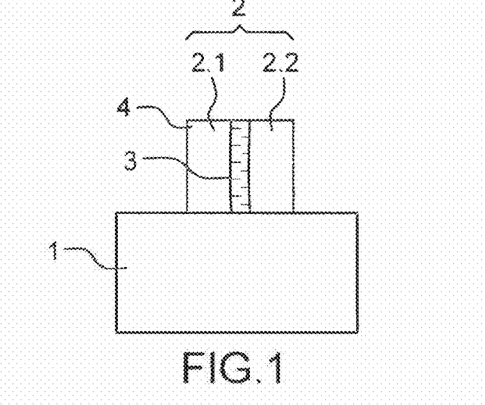
FIG. 1, already described, is a transverse cross-section view of a slotted optical waveguide according to prior art.

Integrated optical sensors for fluid analysis have been rapidly developed over the last years. Indeed, they have many advantages: they are insensitive to electromagnetic interferences, they are versatile and accurate, mechanically and thermally stable. They use optical waveguides the transverse dimensions of which range from a few hundred nanometers to several micrometers. Interaction between light and the fluid to be analysed is made on a depth of a few tens to a few hundreds nanometers. Vertical slotted optical waveguides are for example known from the three papers [1], [2], [3], the references of which are to be found at the end of the description. The optical waveguide includes a base substrate 1 surmounted by a core 2 which takes the form of two parallel rails 2.1, 2.2 bounding between them a slot 3 intended to accommodate the fluid 4. FIG. 1 can be referred to. The core 2 is generally made of a high refractive index material such as silicon nitride, the base substrate 1 being itself generally of silicon. The slot 3 has its cross-section oriented such that its minor side is substantially parallel to the main surface of the base substrate 1 and its major side is substantially perpendicular to the main surface of the base substrate 1. One interest of this structure is that most of the quasi-TE component of the light injected in the waveguide is located in the fluid, which results in an enhanced interaction between the fluid to be analysed on the one hand and the guided light on the other hand. However, one drawback is that the light has to have a wavelength higher than 1.1 nanometer if the substrate is of silicon, such that it is transparent.

In U.S. Pat. No. 7,609,932, the slot has been turned around, the minor side of its cross-section is now substantially perpendicular to the base substrate. The slot is filled with a material transparent at the wavelengths used and is sandwiched between two layers forming the core of the optical waveguide. This transparent material has a refractive index lower than that of the two layers forming the core of the optical waveguide. This configuration is not suitable for fluid analysis. In another configuration, the slot is emptied, at least locally, for the fluid to be able to be introduced. The losses are reduced, the quasi-TM component of light introduced in the optical waveguide is confined in the fluid. But the manufacturing method set out does not enable an optical waveguide with a great length to be obtained, that is several tens centimeters or even several meters because it is difficult to remove the material from the slot without damaging the core layer which surmounts the slot.

But, to be able to analyse, with an acceptable sensitivity, fluids having low molar coefficients at reduced concentrations, relying on the Beer-Lambert Law, a great fluid/light interaction length and thus a sufficiently long optical waveguide have to be available.

Currently, optical waveguides of this type are made by techniques of depositing layers and etching these layers, these techniques being conventional.

DISCLOSURE OF THE INVENTION

One purpose of the present invention is precisely to provide an optical waveguide comprising a channel in particular adapted to fluid analysis with a good sensitivity, even if these fluids have low concentrations and coefficients of molar extinction.

One purpose of the present invention is to provide an optical waveguide which has diffusion or radiation losses less significant than in prior art. The diffusion losses are due to the technology employed, the roughness of the waveguide whereas the radiation losses are due to the curvature of the waveguide.

Another purpose of the invention is to provide an optical waveguide which can measure several tens centimeters, or even several tens meters and which can have a footprint with a side of only a few centimeters.

Another purpose of the invention is to provide an optical waveguide which, when used with fluids, does not have the risk to block the fluid inside the channel and prevent it from flowing.

Yet another purpose of the invention is to provide an optical waveguide which, when used with fluids, is not difficult to fill or empty.

Yet another purpose of the invention is to provide an optical waveguide which, when used with fluids, does not risk to be damaged because of the pressure generated by the fluid.

To achieve this, the present invention suggests to adjoin two substrates each incorporating an optical guiding structure exposed at a surface of these substrates and to provide a channel in either or both optical guiding structures.

More particularly, the present invention provides an optical waveguide including a first substrate incorporating a first optical guiding structure being flushed with a surface of the first substrate, a second substrate incorporating a second optical guiding structure being flushed with a surface of the second substrate, these two substrates being assembled superimposed by theirs surfaces such that the two optical guiding structures face each other and extend in a same direction, a channel being fitted between the first and the second optical guiding structures, directed along said direction, this channel having a cross-section a large dimension of which is substantially parallel to the surface of the first substrate and to the surface of the second substrate, this channel being intended to accommodate a fluid.

The channel can overlap the first optical guiding structure, the second optical guiding structure, or the first and second optical guiding structures.

The first optical guiding structure and the second optical guiding structure are selected from the core of a planar optical waveguide or the core of a stripe optical waveguide.

Advantageously, in particular to improve the lateral containment of the optical signal guided in the waveguide and reduce the power losses caused by possible curvatures of the waveguide, the latter further includes at least one reservoir laterally adjoining the channel and continuously communicating with it substantially throughout the length of the channel.

The optical waveguide can be a straight waveguide, but to be able to benefit from a large length of an optical waveguide with a small footprint, it is preferable that it takes a serpentine shape, a spiral shape or in that it combines two by two or three by three these three shapes.

Alternatively, the optical waveguide could be a ring resonant structure or a Fabry-Pérot resonant structure ending with Bragg or other type reflectors.

It is preferable, to ensure a good circulation of the fluid intended to circulate in the channel, that the channel has a hydrophilic internal surface.

For the same purpose, it is preferable that the reservoir has a hydrophilic internal surface.

Alternatively, the channel could have a hydrophobic internal surface. The reservoir could have a hydrophobic internal surface.

Advantageously, the first substrate and the second substrate will be of glass because glass has a low sensitivity to the optical damage and is easy to work. It has a good chemical resistance and allows co-integration of optical and microfluidic functions.

The present invention also relates to an optical sensor for fluid analysis which includes an optical waveguide thus characterised with two reservoirs on either side of the channel, means for the inlet of fluids in the channel which is connected to one of the reservoirs and means for the outlet of the fluid from the channel which is connected to the other reservoir.

The present invention also relates to a spectrometry device including an optical sensor thus characterised, a light source connected to one end of the optical waveguide and a spectrum analyser connected to the other end of the optical waveguide.

The present invention also relates to a method for manufacturing an optical waveguide comprising a channel including the following steps of:
  forming in a first substrate a first optical guiding structure being flushed with a surface of the first substrate and forming in a second substrate a second optical guiding structure being flushed with a surface of the second substrate;
  forming a channel overlapping the first substrate, the second substrate or the first and the second substrates, this channel being intended to accommodate a fluid;
  turning around one of the substrates from the first substrate and the second substrate;
  aligning and assembling the first substrate to the second substrate by theirs surfaces such that both optical guiding structures are superimposed facing each other and extend in a same direction and that the channel is fitted between the first optical guiding structure and the second optical guiding structure and directed along said direction, this channel having a cross-section a large dimension of which is substantially parallel to the surface of the first substrate and to the surface of the second substrate.

The step of forming the channel occurs before or after the step of forming the first optical guiding structure and before or after the step of forming the second optical guiding structure It is advantageous to provide after the steps of forming the first optical guiding structure, forming the second optical guiding structure, forming the channel and before the step of turning around one of the substrates, a step of forming at least one reservoir laterally adjoining the channel and continuously communicating with it substantially throughout the length of the channel.

The step of forming the first optical guiding structure and the step of forming the second optical guiding structure comprise steps of ion exchange, ion implantation or diffusion, photo-writing or else enabling the refractive index of the first and second substrates to be locally modified.

To improve the fluid circulation, it is advantageous to further provide a treatment step for hydrophilising or hydrophobising an internal surface of the channel and/or an internal surface of the reservoir.

BRIEF DESCRIPTION OF THE DRAWINGS

The present invention will be better understood upon reading the description of exemplary embodiments given by way of purely indicative and in no way limiting purposes, with reference to the appended drawings wherein:

FIGS. 6A1, 6A2, 6B1, 6B2, 6C1, 6C2, 6D1, 6D2, 6E1, 6E2, 6F1, 6F2, 6G1, 6G2, 6H2, 6I1, 6I2 and 6J represent steps of a method for manufacturing an optical waveguide object of the invention;

Identical, similar or equivalent parts in the different figures described hereinafter bear the same reference numerals so as to facilitate switching from one figure to another.

Different parts represented in the figures are not necessarily drawn at a uniform scale, to make the figures more legible.

These different alternative represented should be understood as not being mutually exclusive.

DETAILED DISCLOSURE OF PARTICULAR EMBODIMENTS

Figure 2A:
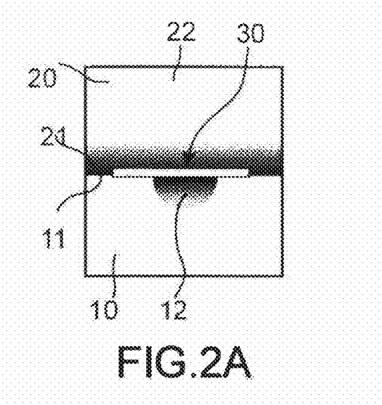
FIGS. 2A, 2B, 2C are transverse cross-section views of several alternative optical waveguides object of the invention.
Figure 2B:
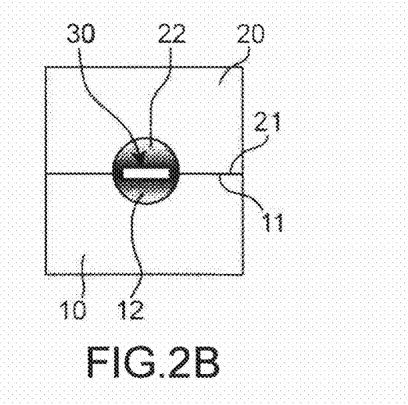
Figure 2C:
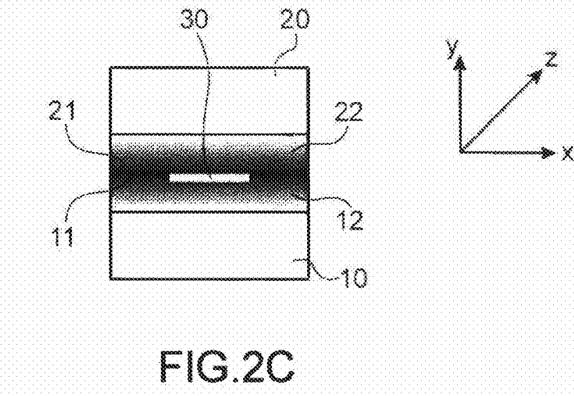

FIGS. 2A, 2B, 2C which show in a transverse cross-section view first examples of an optical waveguide according to the invention will now be referred to. The optical waveguide comprising a channel according to the invention includes a first substrate 10 and a second substrate 20 each having a so-called main surface, respectively 11 and 21. They are joined by their main surfaces 10, 20. The first substrate 10 incorporates a first optical guiding structure 12. This first optical guiding structure 12 is flushed with the surface 11 of the first substrate 10, it is exposed at the surface of the first substrate 10. The first optical guiding structure 12 forms an optical waveguide core and the first substrate 10 an optical waveguide shell, the first substrate incorporating the first optical guiding structure forms a first optical waveguide.

In the example of FIGS. 2A and 2B, the first optical waveguide is a stripe waveguide, in the example of FIG. 2C, it is a planar waveguide.

The second substrate 20 incorporates a second optical guiding structure 22. This second optical guiding structure is flushed with the surface 21 of the second substrate 20, it is exposed at the surface of the second substrate 20. The second optical guiding structure forms a waveguide core and the second substrate an optical waveguide shell, all of them forming a second optical waveguide. Both optical waveguides are adjoining.

In the example of FIGS. 2A and 2C, the second optical waveguide is a planar guide, in the example of FIG. 2B, it is a stripe waveguide.

The first guiding structure and the second guiding structure are superimposed, facing each other and extend in a same direction. This direction is the direction z represented in FIGS. 2A, 2B, 2C. The joined surfaces 11, 21 of the substrates 10, 11 form an interface common to both waveguides.

The refractive index of the first and second optical waveguide structures is higher than that of the substrate in which they are incorporated.

A channel 30 is fitted between the first and second guiding structures. It can be formed in the first guiding structure as in FIG. 2C, in the second optical guiding structure as in FIG. 2A or overlapping both the first optical guiding structure and the second optical guiding structure as in FIG. 2B. The channel 30 extends in the same direction z as the first and second optical guiding structures. The transverse cross-section of the channel 30 has a large dimension substantially oriented in parallel to the surface 11 of the first substrate 10 and to the surface 21 of the substrate 20. The channel 30 has a small dimension substantially perpendicular to these surfaces 11, 21.

The optical guiding structures are intended to propagate light. In an application of fluid analysis, the channel 30 is intended to contain the fluid.

It is possible that the optical waveguide comprising a channel object of the invention is a straight waveguide. FIGS. 3C, 3D, subsequently described, show straight segments 50, 52 of the optical waveguide comprising a channel.

Figure 3A:
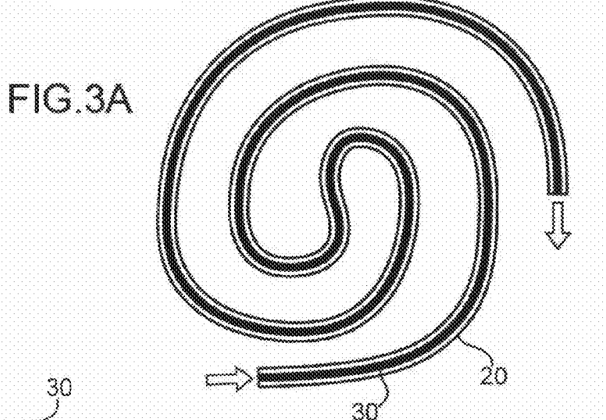
FIGS. 3A, 3B, 3C, 3D are top views of different configurations of an optical waveguide object of the invention.
Figure 3B:
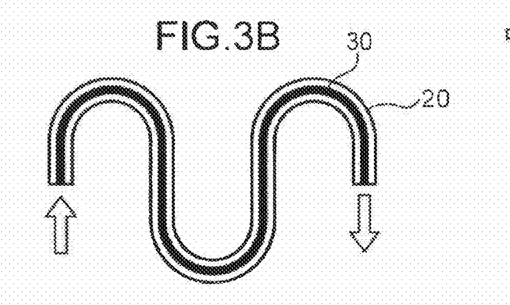
Figure 3C:
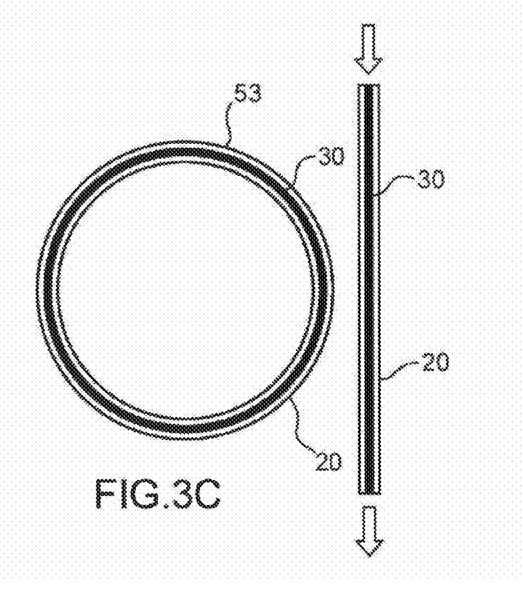
Figure 3D:
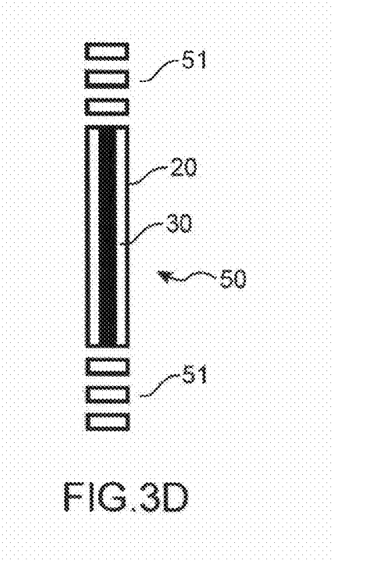

It is preferable, in particular in applications in which it is attempted to have the largest fluid/light interaction length possible, that the optical waveguide comprising a channel is spiral curved as in FIG. 3A, serpentine curved as in FIG. 3B. More particularly in FIG. 3A, it is a double spiral, the optical waveguide being folded as a hairpin and spiraled. Of course, it is possible to combine these three shapes two by two or all three of them.

Alternatively, the optical waveguide comprising a channel object of the invention can form a ring resonant structure as illustrated in FIG. 3C. There is a slotted optical waveguide configured as a ring 53 and a straight segment 52 of a slotted optical waveguide coupled to the ring. The coupling is made by evanescent waves.

Alternatively, the optical waveguide comprising a channel object of the invention can form a Fabry-Pérot resonant structure as illustrated in FIG. 3D. The segment of the optical waveguide comprising a channel, object of the invention, bearing the reference 50 is surrounded at its two ends by Bragg reflectors 51. Alternatively, other types of reflectors could be used, these would be more or less reflective mirrors depending on the desired application. These structures are well-known to those skilled in the art.

It is well known that when a waveguide is curved, part of the guided electromagnetic wave which propagates therein leaks out of the core. These are radiation or curvature losses.

Figure 5A:
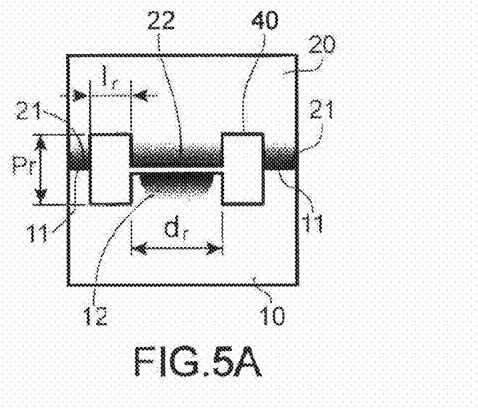
FIGS. 5A, 5B, 5C are transverse cross-sections of several alternative optical waveguides object of the invention equipped with at least one reservoir.
Figure 5B:
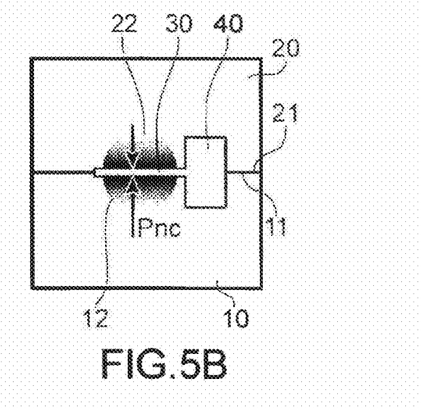
Figure 5C:
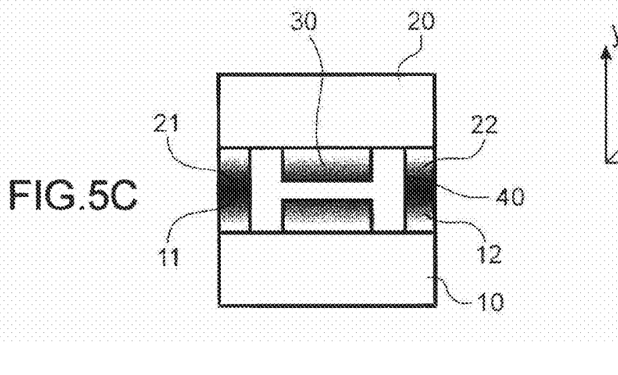

According to an alternative enabling the radiation due to the curvatures to be very efficiently minimized, the optical waveguide comprising a channel object of the invention is equipped with at least one reservoir 40 laterally adjoining the channel 30, which continuously communicates with the channel 30, substantially throughout its length. FIGS. 5A and 5B, 5C can be referred to. FIG. 5B only shows a single reservoir 40 and FIGS. 5A, 5C show two of them which laterally surround the channel 30. The reservoir(s) 40 communicate(s) with the channel 30 at its smallest side. The optical waveguide comprising a channel represented in FIG. 5A is similar to that represented in FIG. 2A, the one represented in FIG. 5B is similar to that represented in FIG. 2B, the one represented in FIG. 5C is similar to that represented in FIG. 2C. The use of a single reservoir 40 has an interest in particular if the waveguide has only a single curvature direction. The reservoir 40 is then placed on a convex edge of the channel 30. One purpose of the reservoir 40 is to increase the lateral containment of the electromagnetic field in the fluid to avoid that it leaks from the curvature.

In FIGS. 5A, 5B, 5C a transverse cross-section of the reservoirs 40 is represented. The large dimension $p_r$ of this cross-section can be substantially perpendicular to the surface of the first and second substrates, whereas the small dimension $I_r$ is oriented substantially parallel to these surfaces. The reverse is possible on the one hand and on the other hand, the cross-section of the reservoir could have two transverse dimensions $p_r$ and $I_r$ substantially equal.

For the presence of the reservoirs 40 to be efficient, of course, they should be sufficiently close to the first and second optical guiding structures 12, 22. Another interest of the reservoir(s) 40 is to facilitate filling and emptying the channel 30, without exerting a pressure leading to a deformation or damage to the waveguide. In particular, in the presence of two reservoirs 40, a continuous flow of the fluid in the channel 30 can be ensured, even if the channel is curved, by injecting the fluid in one of the reservoirs and by extracting it therefrom, for example with a pump of the other reservoir. Alternatively, the fluid could be injected in both reservoirs or even two fluid sources could be injected in each of the reservoirs in a separated manner.

Another purpose of the reservoir(s) 40 is to enable the channel to be filled without exerting external pressures and restricting the capillary pressure. Yet another purpose of the reservoir(s) is to enable the channel to be filled without setting a significant hydrodynamic flux of the entire fluid sample in the optical coupling zone. Yet another purpose of the reservoir(s) 40 is to reduce the sensitivity of the waveguide to plugging problems.

When a fluid analysis is made with the optical waveguide comprising a channel object of the invention, a first fluid can be switched to a second fluid without stopping the measurement, the flow is continuous, the first fluid being wholly replaced by the second fluid after some time. The presence time of the first fluid in the channel depends, among other things, on the distance between both reservoirs. The content of each reservoir may not be identical.

Maximum dimensions that can have the cross-section of the channel 30 and the reservoirs 40 will now be given by way of non-limiting example. These dimensions are marked in FIGS. 5A and 5B. The large dimension $d_r$ or width of the transverse cross-section of the channel 30 is advantageously lower than or equal to 100 micrometers. It corresponds to the spacing between both reservoirs 40. The small dimension $p_{nc}$ or depth of the channel 30 is advantageously lower than or equal to 100 nm. It can fall to one nanometer. The method for manufacturing the waveguide comprising a channel that will now be described allows it. This was not the case of waveguides of the previously mentioned documents of prior art. The dimensions just given are perfectly suitable for use as a slotted waveguide configuration, but for an evanescent wave-type configuration, these transverse dimensions can be larger. Indeed, integrated absorption spectrometry is also used with evanescent wave sensors.

The transverse dimensions of the reservoirs $p_r$ and $I_r$ will be advantageously higher than or equal to one micrometer in order to preserve one of the main purposes of the reservoirs, mainly the pressure relief exerted by the fluid.

Figure 4:
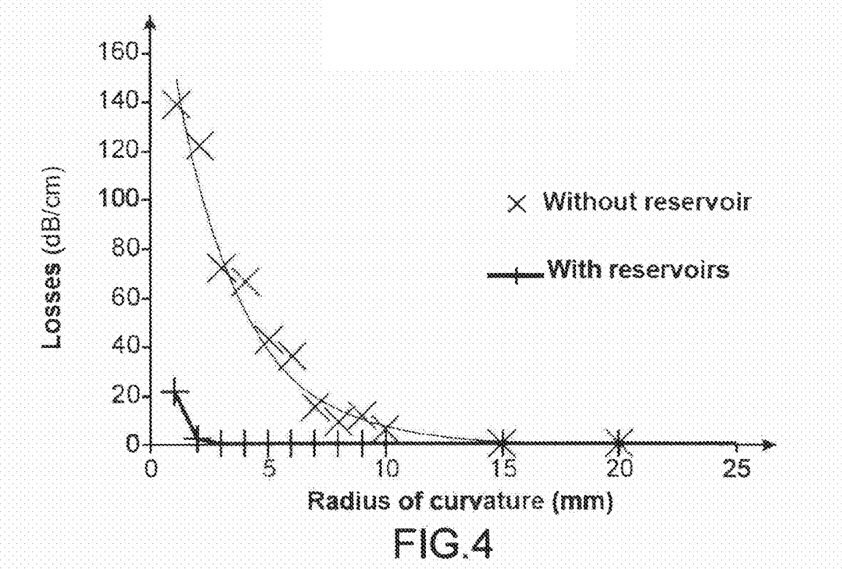
FIG. 4 illustrates the radiation losses as a function of the radius of curvature of optical waveguides of the invention provided or not with reservoirs.

In FIG. 4 is represented a graph illustrating the curvature losses (in dB/cm) as a function of the radius of curvature of the waveguide comprising a channel object of the invention. These losses are expressed for a waveguide comprising a channel free of reservoirs and for a waveguide comprising a channel provided with two reservoirs. The darkest continuous curve is an exponential function which passes through most of the crosses corresponding to the losses of the optical waveguide free of reservoirs.

These losses have been obtained by simulation, using a software implementing the AFMM (Aperiodic Modal Fourier Method). For this simulation, an optical waveguide comprising a channel object of the invention has been used, the above explained dimensions of which are the following ones:

Channel: $d_r$=30 micrometers and $p_{nc}$=100 nanometers.
Reservoirs: $I_r$=1 micrometer and $p_r$=2 micrometers.

It is noted that with the optical waveguide with reservoirs, a radius of curvature of 3 mm enables a loss level lower than 0.5 dB/cm to be obtained whereas a radius of curvature cannot be lower than 15 mm to reach this loss level with an optical waveguide without reservoirs. The losses are considered as negligible if they are lower than or equal to 0.5 dB/cm. In the double spiral structure illustrated in FIG. 3A, the critical radius of curvature Rmin of the optical waveguide at the folded part thereof should not be lower than 3 mm for the optical waveguide with reservoirs and lower than 15 mm for the optical waveguide without reservoirs. This enables to have a much higher interaction length with the reservoirs for a same footprint as if there were only a single spiral.

An exemplary method for manufacturing an optical waveguide object of the invention will now be described referring to FIGS. 6A1-6A2 to 6I1-6I2 and 6J.

Figure 6A:
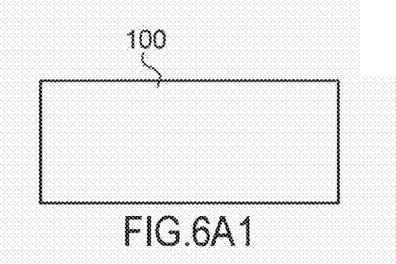
Figure 6A:
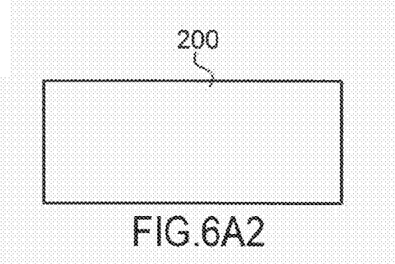
Figure 6B:
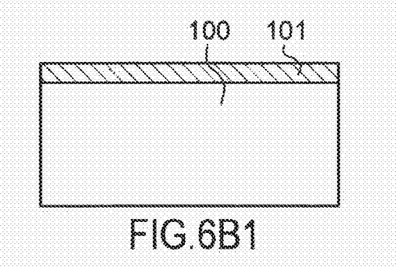
Figure 6B:
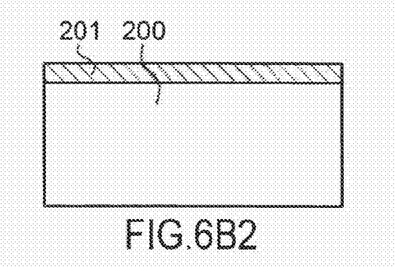

First, there is a first substrate 100 and a second substrate 200 of glass, for example (FIGS. 6A1 and 6A2). Glass is an interesting material in this application because of its low sensitivity to optical damage, strength, stability and versatility in terms of chemical treatments. Substrates 100, 200 having a not very rough surface condition are chosen to be compatible with microelectronics. Alternatively, these substrates 100, 20c could be of a semi-conductor material as silicon or of polymeric plastic material or any other material suitable for waveguides. A surface of each of the substrates is coated with a mask; the masks are respectively referenced 101, 201 (FIGS. 6B1, 6B2). The masks 101, 201 can be of aluminium or any other material being impervious to the exchanged ions.

Figure 6C:
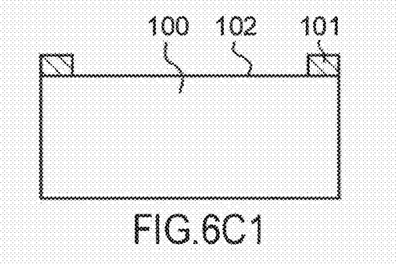
Figure 6C:
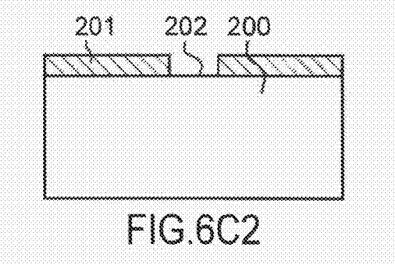

A window 102, 202 is opened in each of these masks 101, 201, generally by lithography (FIGS. 6C1 and 6C2). The limit of the window 102, 202 aims at bounding the boundary of a first optical guiding structure on the first substrate and the boundary of a second optical guiding structure on the second substrate.

Figure 6D:
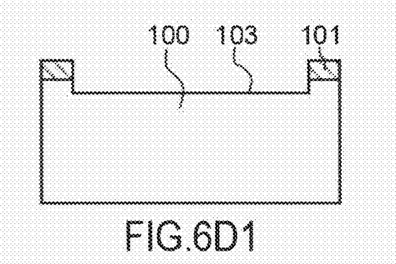

In the window 102 of at least one mask 101, an etching step aiming at attacking the surface of the substrate 100 so as to dig the channel 103 can be carried out. This etching step (FIG. 6D1) can be an etching through micromachining, wet or dry chemical etching. This step provides the channel with at least its depth, its surface dimensions will be the final ones or could be subsequently reworked if there is a formation of reservoirs. The mask could also be dispensed with and the channel could also be dug by laser ablation.

Figure 6D:
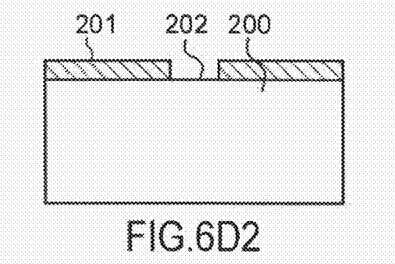

In the example described, the channel 103 is only dug in the first substrate 100. The second substrate 200 thus has not been modified between FIG. 6C2 and FIG. 6D2.

This etching step could be made in the second substrate only or even in both substrates.

Figure 6E:
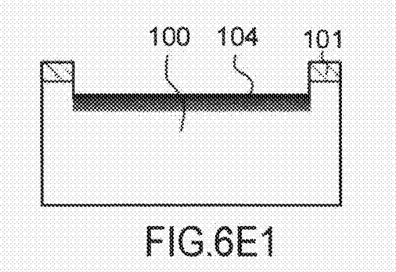

In each of the substrates 100, 200, an optical guiding structure 104, 204 flushed with the surface of the substrates 100, 200 will be created. This can be made by ion exchange at the surface of each of the substrates 100, 200 (FIGS. 6E1, 6E2). Both substrates 100, 200 thus masked can be dipped in a molten salt bath, containing for example, $Ag^+$ or $K^+$ or even $Tl^+$ cations. At the places of the windows 102, 202, there will be an exchange between the $Na^+$ cations of the glass and the cations of the salt bath. This causes a rise in the refractive index in the exposed zone and results in the formation of an optical guiding structure 104, 204 the surface dimensions of which depend on the dimensions of the window 102, 202 provided in the mask 101, 201. The lateral dimensions of the optical guiding structures will be able to be adjusted if reservoirs are provided.

Other methods can be employed to form the optical guiding structure as ion implantation or diffusion, photo-writing or any other method able to locally modify the refractive index of the first and second substrates.

The step of forming the optical guiding structures and that of forming the channel can be reversed. The channel extends at least partially in the optical guiding structures. In the first substrate 100, the optical guiding structure 104 is a planar guiding structure and in the second substrate 200, the optical guiding structure 204 is a stripe guiding structure.

Figure 6F:
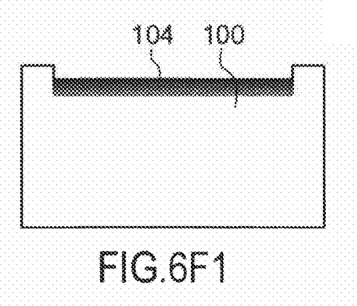
Figure 6F:
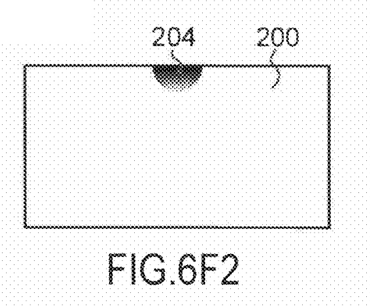

The following step is a step of withdrawing both masks (FIGS. 6F1, 6F2).

Figure 6G:
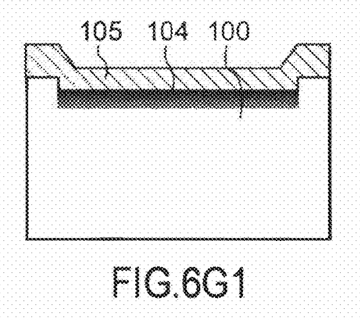
Figure 6G:
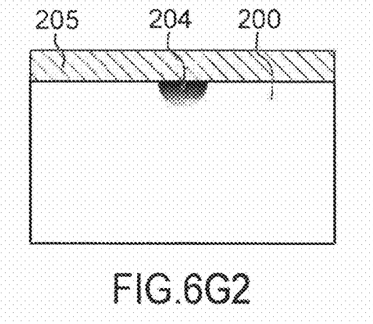
Figure 6H:
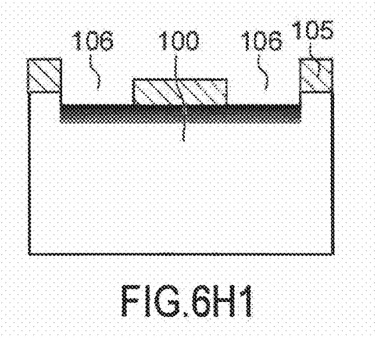
Figure 6H:
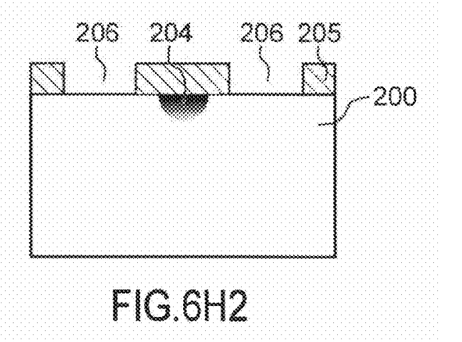
Figure 6I:
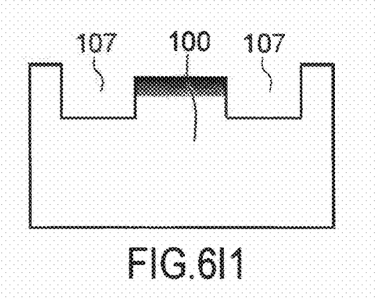
Figure 6I:
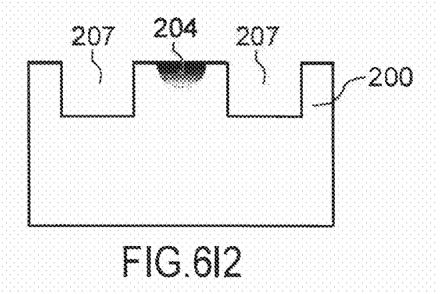
Figure 6J:
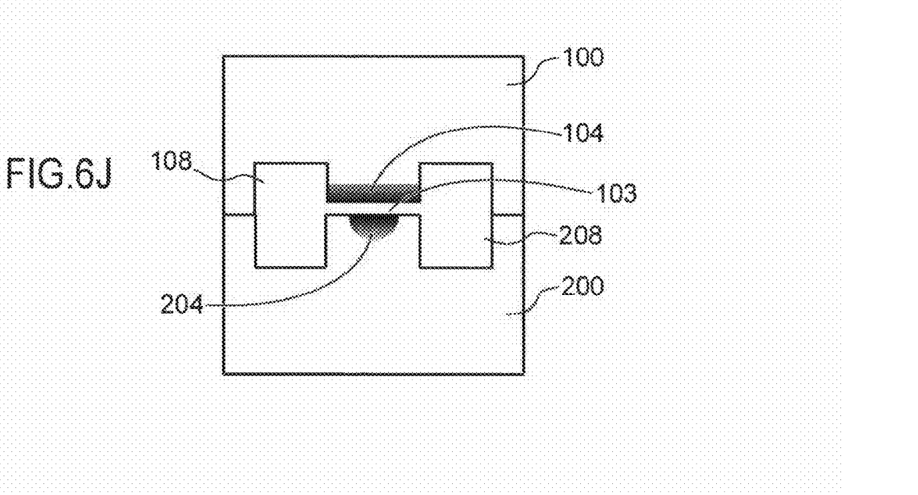

If the optical waveguide comprising a channel does not have a reservoir, it is sufficient to turn around one of the substrates, to align them with respect to the other such that both optical guiding structures 104, 204 are superimposed facing with each other and to assemble both substrates to each other. Both optical guiding structures 104, 204 then extend in a same direction. This assembly can be made by molecular bonding, anodic, thermal or chemical bonding. This step is not illustrated in this configuration. FIG. 6J could be referred to so as to illustrate the alignment and assembly.

If one or more reservoirs are provided, a mask 105, 205 is again deposited at the surface of each of both substrates 100, 200 (FIGS. 6G1, 6G2). The mask material depends on the etching method: it can be aluminium, alumina, chromium, resin for example.

They are opened by lithography so as to form the windows 106, 206 at the perimeter of the reservoirs, these reservoirs being finally provided on either side of the channel 104 which in this example will be laterally reduced. This step of opening the windows is illustrated in FIGS. 6H1, 6H2. The reservoirs also communicate with the channel continuously over the length of the channel. The substrates 100, 200 are etched in depth at the windows 106, 206 of the masks 105, 205. This step of etching the reservoirs can be, as the step of etching the channel, an etching by micromachining, by wet or dry chemical etching for example. Laser ablation can be used, and once again the mask is no longer necessary. In each substrate 100, 200, only a portion of the reservoir 107, 207 is etched (FIGS. 6I1, 6I2). The reservoirs 108, 208 will be only finalized during the assembly of both substrates 100, 200 by superimposing two portions of the reservoirs 107 and 207 facing each other. Etching reservoir portions in the first substrate results in reducing the width of the channel 104. It also facilitates subsequent alignment of both substrates.

Then the masks associated with the reservoirs are removed (FIGS. 6I1, 6I2).

The only thing remaining is to assemble both substrates 100, 200 by turning around one of them and aligning as previously described (FIG. 6J).

A step of treating the surfaces of these substrates, aiming at hydrophilising the internal surfaces of the channel and of the reservoirs can be provided, if the fluid to be analysed is an aqueous phase.

Other treatments can be contemplated, for example to hydrophobise the internal surfaces of the channel and of the reservoirs, if the fluid to be analysed is an aqueous phase. The choice of the property to be given to these surfaces depends on the fluid used.

These treatments are not a problem for those skilled in the art.

A rinsing of the substrates and a drying are then required. A hydrophilic surface will enable the fluid to be better spread and will facilitate flowing thereof. It is possible that this treatment step only regards the channel 104, it can occur previously, for example, after the step illustrated in FIGS. 6F1, 6F2 but before the step of depositing a mask illustrated in FIGS. 6G1, 6G2.

It is preferable to provide a step of washing the substrates just before each step of depositing the mask and before the final assembly of both substrates.

Suitable washing methods are numerous and they are not a problem for those skilled in the art.

Figure 7:
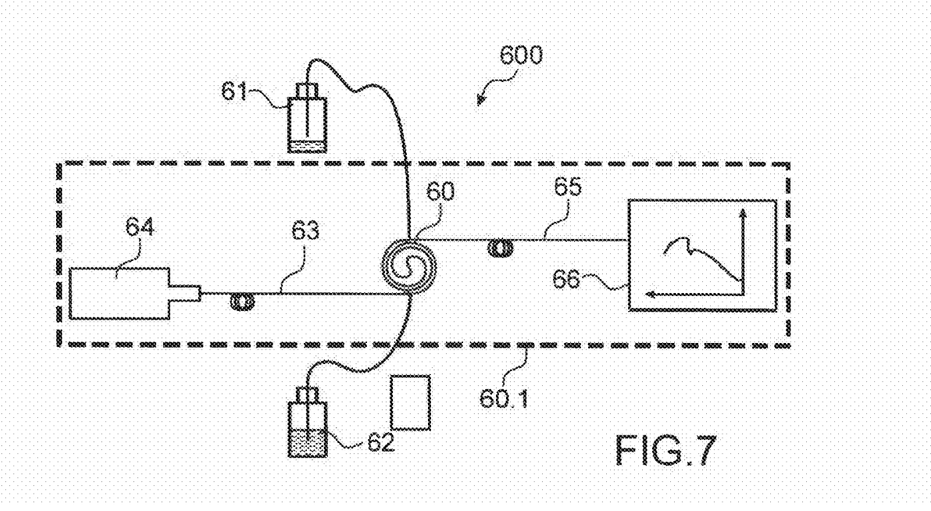
FIG. 7 illustrates an optical sensor for fluid analysis using an optical waveguide according to the invention and a spectrometry device including such an optical sensor.

A fluid analysis device by spectrometry object of the invention will now be described referring to FIG. 7. This device includes an optical sensor 600 including an optical waveguide 600 comprising a channel 60 according to the invention cooperating with a fluid inlet device 61 and a fluid outlet device 62. The sensor can be an evanescent wave sensor.

In this figure, the optical waveguide comprising a channel 60 is arranged as a double spiral. The spiral is represented and it is assumed that part of the upper substrate (or superstrat) has been removed. Of course, the waveguide could take another form: as a serpentine or a straight line in particular if a high sensitivity is not needed.

The optical waveguide comprising a channel 60 is laterally provided, on each side of the channel, with reservoirs communicating with it. The reservoirs are not visible. One of the reservoirs is connected to fluid inlet means 61. The other reservoir is connected to fluid outlet means 62. At least one of the fluid inlet means and fluid outlet means can integrate a suction or injection pump (not represented). These fluid inlet or fluid outlet means 61, 62 take the form of vials. Alternatively, it could be syringes for example. Continuous fluid flux measurements can be carried out without worrying about a fluid blockage in the channel or a damage to the channel due to a very high fluid pressure.

One of the ends of the optical waveguide comprising a channel 60 is connected via an optical fibre 63 to a light source 64 such as a laser diode, a super-luminescent diode, a laser, a super-continuum laser source, a white light source. What is important in the choice of the light source 64 is that it has a sufficient power for a signal to be detected at the output of the optical waveguide comprising a channel and that its wavelength range is adapted to the fluid to be analysed. A white light source and a super-continuum laser source are particularly interesting because they can cover a wavelength range of several hundreds nanometers.

The other end of the optical waveguide comprising a channel 60 is connected via another optical fibre 65 to a spectrum analyser 66. Both optical fibres 63, 65 are adapted to the light source 64. They are connected to the light source 64 and to the optical waveguide comprising a channel 60 for the first one and to the optical waveguide comprising a channel 60 and to the spectrum analyser 66 for the other with appropriate connectors.

The light source 64, the optical waveguide comprising a channel 60 and the spectrum analyser 66 can be integrated on a same chip 60.1.

Such a spectrometry device can be used to perform molecular spectrometry, absorption spectrometry, fluorescence spectrometry or colorimetry. The optical sensor object of the invention can be generally used in chemistry, for analysing separation processes in nuclear industry, for analysing fluids such as waste oils or polluted water, to make volumetric titrations, pH measurements. In biology, it can be used to unwind DNA strands. Other applications are contemplatable, for example, to make atmospheric pollution measurements.

Increasing interaction length between the fluid and light by curving the optical waveguide comprising a channel enables the sensitivity of the sensor to be increased without introducing additional losses. It can be used with a variety of fluids.

Although several embodiments of the invention have been represented and described in a detailed manner, it will be understood that different changes and modifications can be provided without departing from the scope of the invention. In particular, other etching and depositing methods already developed and known to those skilled in the art can be employed.

RECITED DOCUMENTS

[1] « Slot-waveguide biochemical sensor », C. A. Barrios et al., Optics Letters/Vol. 32, N°21/Nov. 1, 2007, pages 3080-3082.

[2] "Guiding and confining light in void nanostructure" V. R. Almeida, Jun. 1, 2004/Vol. 29, N°11/Optics Letters, pages 1209-1211.

[3] "Demonstration of slot-waveguide structures on silicon nitride/silicon oxide platform" C. A Barrios et al., May 28, 2007/Vol. 15, N°11/Optics Express, pages 6846-6856.

The invention claimed is:

1. An optical waveguide comprising:
a first substrate incorporating a first optical guiding structure being flushed with a surface of the first substrate;
a second substrate incorporating a second optical guiding structure being flushed with a surface of the second substrate;
the first and second substrates being assembled superimposed by theirs surfaces such that the first and second optical guiding structures face each other and extend in a same direction;
a channel being fitted between the first and the second guiding structures, directed along the direction, the channel having a cross-section a large dimension of which is substantially parallel to the surface of the first substrate and to the surface of the second substrate, the channel configured to accommodate a fluid.

2. The optical waveguide according to claim 1, wherein the channel overlaps the first optical guiding structure, the second optical guiding structure, or the first and second optical guiding structures.

3. The optical waveguide according to claim 1, wherein the first optical guiding structure and the second optical guiding structure are selected from a core of a planar optical waveguide or a core of a stripe optical waveguide.

4. The optical waveguide according to claim 1, further comprising at least one reservoir laterally adjoining the channel and continuously communicating with the channel substantially throughout a length of the channel.

5. The optical waveguide according to claim 1, having a straight shape, a serpentine shape, a spiral shape, or combining two by two or three by three these three shapes.

6. The optical waveguide according to claim 1, forming a ring resonant structure or a Fabry-Perot resonant structure ending with Bragg or other type reflectors.

7. The optical waveguide according to claim 1, wherein the channel has a hydrophilic or hydrophobic internal surface.

8. The optical waveguide according to claim 4, wherein the reservoir has a hydrophilic or hydrophobic internal surface.

9. The optical waveguide according to claim 1, wherein the first substrate and the second substrate are made of glass.

10. An optical sensor for fluid analysis comprising an optical waveguide according to claim 4, with two reservoirs on either side of the channel, means for inlet of fluids in the channel which is connected to one of the reservoirs and means for outlet of the fluid from the channel which is connected to the other reservoir.

11. A spectrometry device comprising an optical sensor according to claim 10; a light source connected to a first end of the optical waveguide; and a spectrum analyzer connected to a second end of the optical waveguide.

12. A method for manufacturing an optical waveguide with a channel comprising:

forming, in a first substrate, a first optical guiding structure being flushed with a surface of the first substrate and forming, in a second substrate, a second optical guiding structure being flushed with a surface of the second substrate;

forming a channel overlapping the first substrate, the second substrate or the first and the second substrates, the channel configured to accommodate a fluid;

turning around one of the substrate from the first substrate and the second substrate;

aligning and assembling the first substrate to the second substrate by their surfaces such that first and second optical guiding structures are superimposed facing each other and extend in a same direction and the channel is fitted between the first optical guiding structure and the second optical guiding structure and directed along the direction, the channel having a cross-section a large dimension of which is substantially parallel to the surface of the first substrate and to the surface of the second substrate.

13. The method according to claim 12, wherein the forming the channel occurs before or after the forming the first optical guiding structure and before or after the forming the second optical guiding structure.

14. The method according to claim 12, further comprising, after the forming the first optical guiding structure, forming the second optical guiding structure, forming the channel and before the turning around one of the substrates, forming at least one reservoir laterally adjoining the channel and continuously communicating with the channel substantially throughout a length of the channel.

15. The method according to claim 13, wherein the forming the first optical guiding structure and the forming the second optical guiding structure comprise ion exchange, ion implantation or diffusion, photo-writing or enabling refractive index of the first and second substrates to be locally modified.

16. The method according to claim 13, further comprising a treatment for hydrophilising or hydrophobising an internal surface of the channel and/or an internal surface of the reservoir.

* * * * *